(12) United States Patent
Wong et al.

(10) Patent No.: US 9,568,454 B2
(45) Date of Patent: Feb. 14, 2017

(54) METHODS OF SEPARATING LIPIDS

(71) Applicant: Waters Technologies Corporation, Milford, MA (US)

(72) Inventors: Stephen Wong, Singapore (SG); Mark Ritchie, Singapore (SG)

(73) Assignee: Waters Technologies Corporation, Milford, MA (US)

( * ) Notice: Subject to any disclaimer, the term of this patent is extended or adjusted under 35 U.S.C. 154(b) by 183 days.

(21) Appl. No.: 14/250,622

(22) Filed: Apr. 11, 2014

(65) Prior Publication Data

US 2014/0338432 A1    Nov. 20, 2014

Related U.S. Application Data

(60) Provisional application No. 61/811,559, filed on Apr. 12, 2013.

(51) Int. Cl.
| | |
|---|---|
| *G01N 33/92* | (2006.01) |
| *B01D 15/30* | (2006.01) |
| *G01N 30/34* | (2006.01) |
| *G01N 30/72* | (2006.01) |
| *H01J 49/00* | (2006.01) |
| *G01N 30/36* | (2006.01) |
| G01N 30/02 | (2006.01) |
| G01N 30/06 | (2006.01) |
| G01N 30/88 | (2006.01) |

(52) U.S. Cl.
CPC ......... *G01N 30/7233* (2013.01); *B01D 15/305* (2013.01); *G01N 30/36* (2013.01); *G01N 33/92* (2013.01); *G01N 30/06* (2013.01); *G01N 30/34* (2013.01); *G01N 2030/027* (2013.01); *G01N 2030/062* (2013.01); *G01N 2030/8813* (2013.01); *H01J 49/00* (2013.01); *Y10T 436/24* (2015.01)

(58) Field of Classification Search
CPC ............ B01D 15/305; G01N 2030/027; G01N 2030/062; G01N 2030/8813; G01N 30/02; G01N 30/06; G01N 30/34; G01N 30/36; G01N 30/72; G01N 30/7233; G01N 33/48; G01N 33/49; G01N 33/92; H01J 49/00; Y10T 436/24; Y10T 436/25; Y10T 436/25375; Y10T 436/255

USPC .......... 436/63, 71, 161, 173, 174, 177, 178; 422/70; 210/656, 198.2; 73/61.52, 61.53, 73/61.58

See application file for complete search history.

(56) References Cited

U.S. PATENT DOCUMENTS

| | | | | |
|---|---|---|---|---|
| 2013/0203176 A1* | 8/2013 | Maeba | ................... | G01N 33/92 436/71 |
| 2014/0338429 A1* | 11/2014 | Isaac | ................... | B01D 15/327 73/61.52 |

FOREIGN PATENT DOCUMENTS

WO     2011/152519     * 12/2011

OTHER PUBLICATIONS

Cutignano et al. Prostoglandins and other Lipid Mediators, vol. 93, Jun. 26, 2010, pp. 25-29.I.*
Wormer et al. Organic Geochemistry, vol. 59, Mar. 20, 2013, pp. 10-21.*
Becker et al. Organic Geochemistry, vol. 61, Jun. 5, 2013, pp. 34-44.*

* cited by examiner

*Primary Examiner* — Maureen Wallenhorst
(74) *Attorney, Agent, or Firm* — Locke Lord LLP; Nicholas J. DiCeglie, Jr.

(57) ABSTRACT

The invention provides novel, simple, reliable and effective methods for separating various lipids from biological samples. In certain embodiments, the invention provides HILIC-based UHPLC separation methods. In one embodiment, the methods of the invention offer an efficient and rapid separation of ether glycophospholipids (e.g., plasmalogens) from their diacyl or monoacyl counterparts within the same lipid class. In certain instances, the invention relates to the use of a Waters ACQUITY UPLC® system.

14 Claims, 8 Drawing Sheets

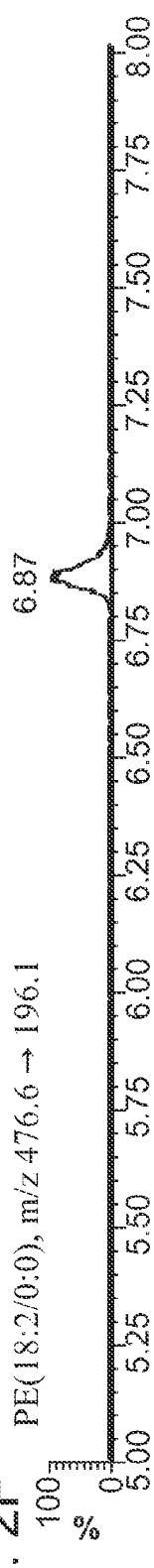
FIG. 2F  PE(18:2/0:0), m/z 476.6 → 196.1
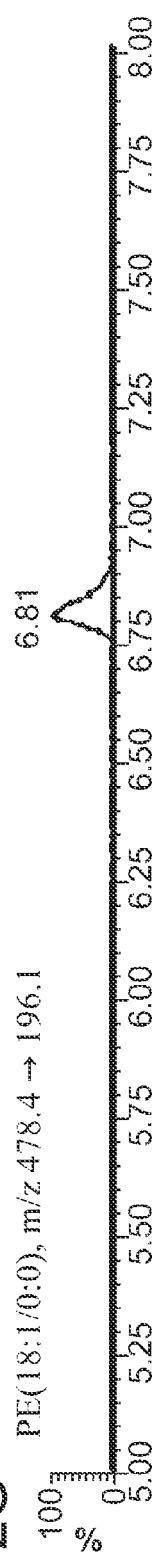
FIG. 2G  PE(18:1/0:0), m/z 478.4 → 196.1
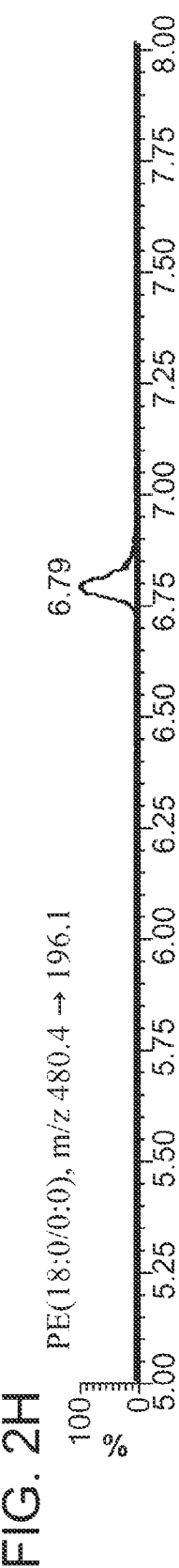
FIG. 2H  PE(18:0/0:0), m/z 480.4 → 196.1
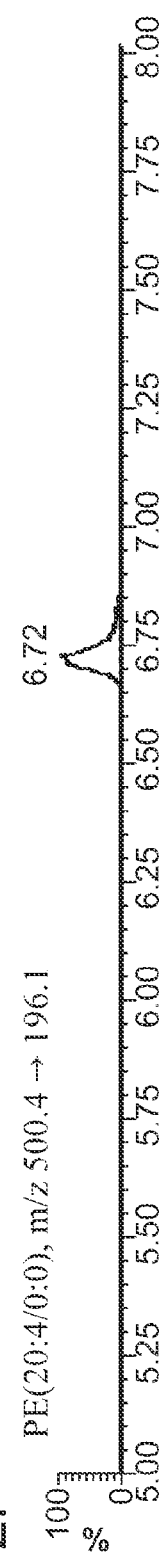
FIG. 2I  PE(20:4/0:0), m/z 500.4 → 196.1
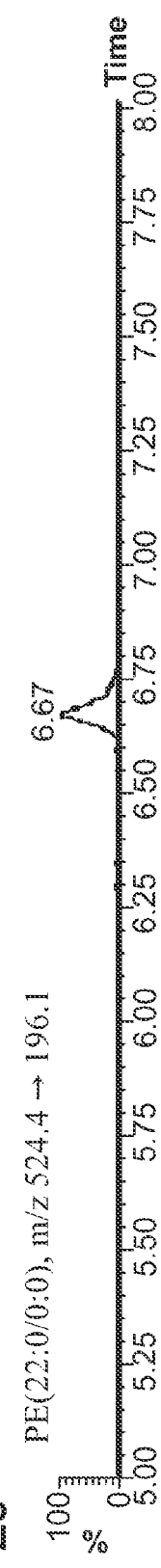
FIG. 2J  PE(22:0/0:0), m/z 524.4 → 196.1

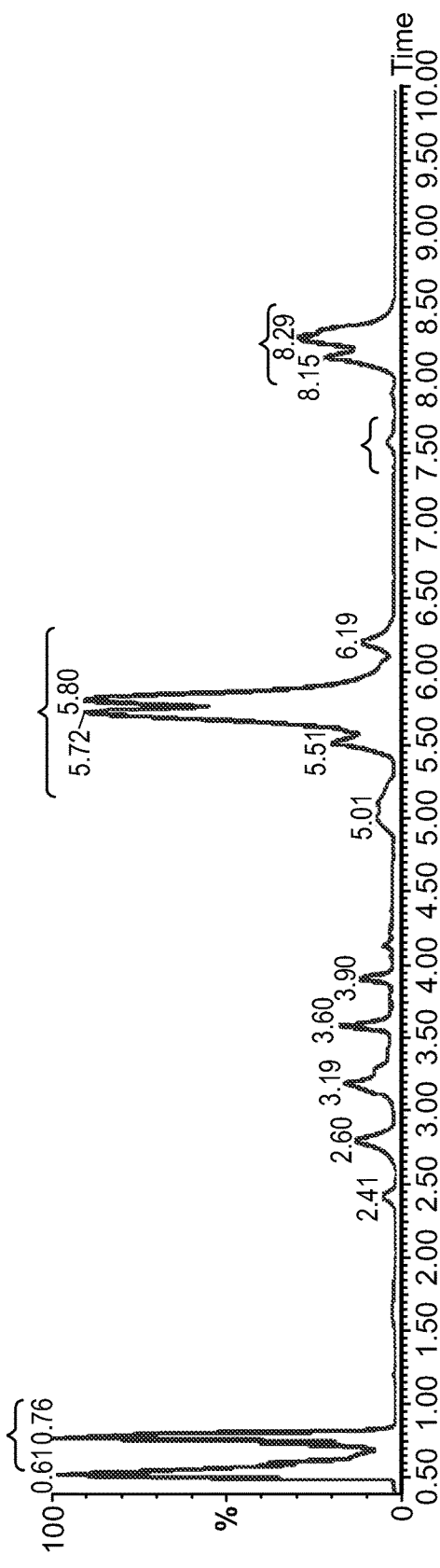
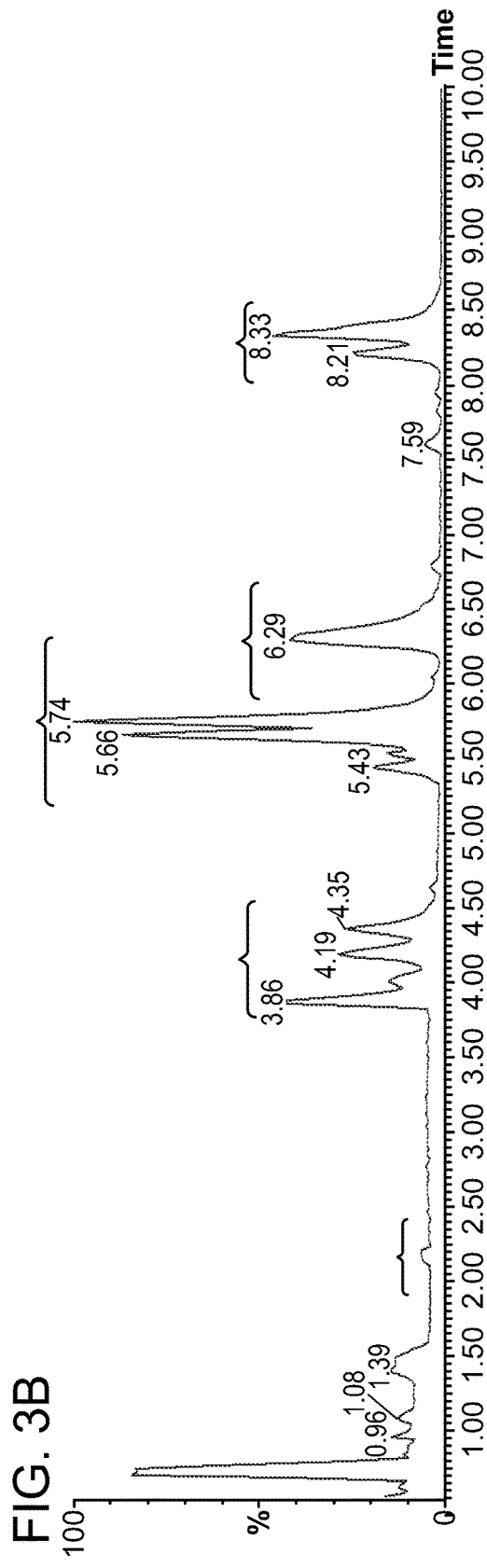
FIG. 3A
FIG. 3B

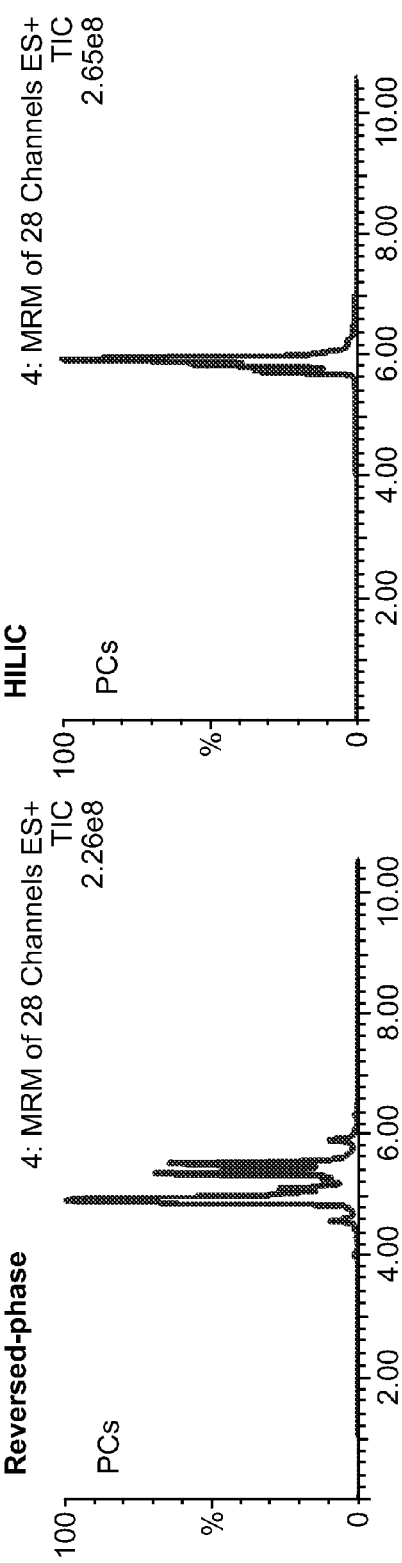
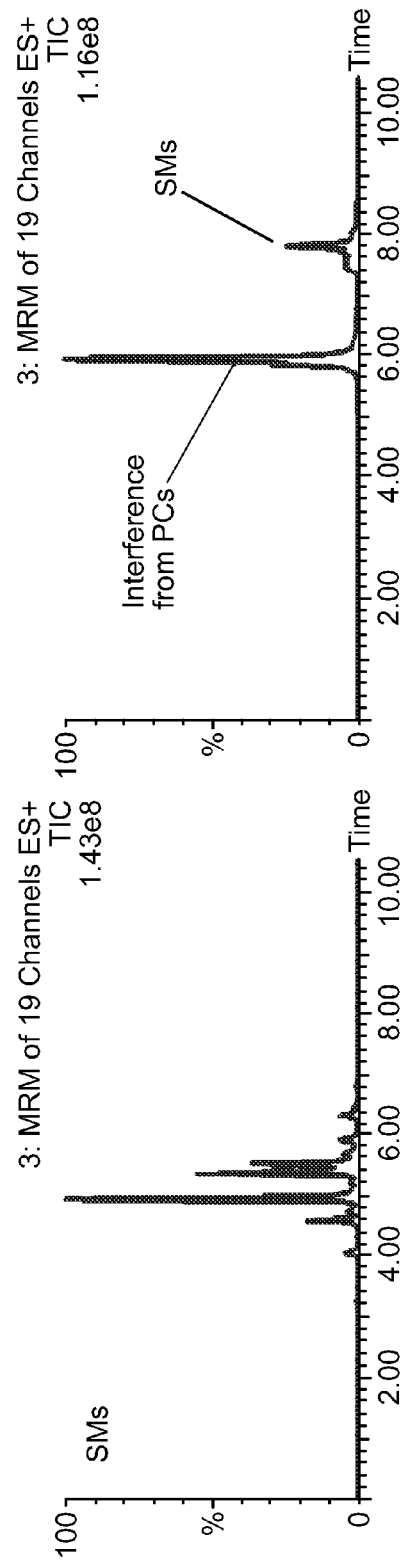

METHODS OF SEPARATING LIPIDS

CROSS REFERENCE TO RELATED APPLICATIONS

This application claims the benefit of priority of U.S. Provisional Patent Application No. 61/811,559, filed Apr. 12, 2013, the disclosure of which is expressly incorporated herein by reference thereto.

BACKGROUND OF THE INVENTION

Lipids are essential in maintaining cell structures, and are believed to play important roles in energy storage and cellular signalling. It is further believed that lipids are important in the pathophysiology of diseases, such as, cancer, neurodegenerative diseases, infections, diabetes etc. Thus, there is an understanding that studies on the lipids could further our understanding of mechanisms of diseases, including the identification of biomarkers and potential drug targets. However, due to their chemical and structural complexity, low concentrations, and complicated properties, there is a major analytical challenge to separate and characterize lipids of various classes from a biological sample.

Among the lipids, plasmalogens, a class of phospholipids, are widespread in human tissues, consisting of approximately 18% of all the phospholipids in a human body (Hermetter A., *Comments Mol. Cell Biophys.* 1988; 5:133-149). Plasmalogens are structural membrane components and a reservoir for secondary messengers. It is believed that plasmalogens are involved in membrane fusion, ion transport, and cholesterol efflux. Further, plasmalogens are believed to be a cell internal antioxidant, scavenging reactive oxygen species (Brosche T et al., *Exp. Gerontol.* 1998; 33:363-9). Despite of the importance recognized with plasmalogens, there has been very limited progress in understanding the exact role and action of plasmalogens due to their poor separation and characterization from other lipids.

Clearly, there is a need for the development of a simple and effective analytical method for separating lipids of different classes (especially, plasmalogens) from biological samples.

SUMMARY OF THE INVENTION

This invention provides novel, simple, reliable and effective methods for separating various lipids from biological samples. In certain embodiments, the separation is achieved, in part, based on head-groups contained in polar lipids. Thus, the methods of the invention achieve efficient separation of phospholipids of various classes, which permits unequivocal characterization and assignment of lipid classes.

In one aspect, the invention provides a method of separating lipids of different classes from a biological sample. The method comprises steps of
i) preparing a biological sample;
ii) loading said biological sample onto an ultrahigh performance liquid chromatography (UHPLC) system, wherein said UHPLC system comprises a hydrophilic interaction chromatography (HILIC) column;
iii) eluting said UHPLC system with an elution solvent; and
iv) detecting lipids of different classes by using a detector (e.g., a mass spectrometer).

In another aspect, the invention provides a method of separating ether glycophospholipids from a biological sample. The method comprises steps of
i) preparing a biological sample;
ii) loading said biological sample onto an ultrahigh performance liquid chromatography (UHPLC) system, wherein said UHPLC system comprises a hydrophilic interaction chromatography (HILIC) column;
iii) eluting said UHPLC system with an elution solvent; and
iv) detecting the ether glycophospholipids by using a detector (e.g., a mass spectrometer).

In certain embodiments, the ether glycophospholipids are plasmalogens.

In certain embodiments, the HILIC-based UHPLC approach of the invention uses a normal phase separation system.

In certain embodiments, the invention relates to the use of a Waters ACQUITY UPLC® system.

The HILIC column can use any polar solid phase surface chemistry, including, but not restricted to simple silica, silica silanol or diol, amide, amino or anionic, cationic or zwitterionic materials, and bound to any type of packing material, e.g., monolithic, porous, solid, pellicular (fused/solid-core, semiporous) or composite beads. For example, the HILIC column used herein is a Waters ACQUITY BEH HILIC (1.7 $\mu$m, 2.1×100 mm) column.

In certain embodiments, the elution solvent used herein is obtained by mixing at least two mobile phases in situ. For example, a first mobile phase (A) and a second mobile phase (B) can be mixed in situ to obtain a solvent used for eluting lipids from the column. In certain embodiments, the volume ratio of the second mobile phase to the first mobile phase is in a gradient that increases during the elution step.

In certain embodiments, each of the mobile phases for preparing the elution solvent comprises acetonitrile and water. For instance, the first mobile phase (A) comprises 95:5 by volume of acetonitrile:water, and the second mobile phase (B) comprises 50:50 by volume of acetonitrile:water.

It is believed that the invention achieves efficient separation through a quick elution and equilibration process. In certain embodiments, the gradient (v/v) of one mobile phase to another is accomplished within about 10 minutes. In one example, the gradient is from 0 to 20% (v/v).

In certain embodiments, the pH value of the elution solvent used herein is higher than 7 (e.g., a pH of 8.0). The elution solvent may further comprise salts, such as, ammonium acetate.

According to the invention, the detector that can be used is a mass spectrometer. Exemplified mass spectrometers include LC-MS/MS, MALDI-MS, tandem quadrupole mass spectrometer, and ESI-MS, or a combination thereof.

The methods of the invention can be applied in separating lipids from biological samples, such as, blood, plasma, urine, body tissue, and a lipid extract from cells or tissues. The cells or tissues can be those obtained from animals, bacteria, plants, or fungi.

The methods of the invention may further include further separation and/or characterization steps of the lipids that have been separated and/or detected by using instrumental systems, such as, off-line 2D LC system, nanoUHPLC system, UHPLC system, LC-MS/MS, mass spectrometry, MALDI-MS, ESI-MS, nuclear magnetic resonance, infrared analysis, flow injection analysis, capillary electrochromatography, ultraviolet detection or a combination thereof.

The methods of the invention may be used to separate lipids from all kinds of biological samples.

BRIEF DESCRIPTION OF THE DRAWINGS

FIG. 3 a-b) are chromatograms of lipid classes extracted from monkey plasma: a) ESI-+chromatogram; and b) ESI-HILIC UHPLC chromatogram.

FIGS. 5 a-b) show summed MRM transitions for 28 phosphatidylcholines (PCs) and 19 sphingomyelins (SMs) as observed by a). reversed-phase UHPLC; and b). HILIC-UHPLC.

DETAILED DESCRIPTION OF THE INVENTION

Figure 1:
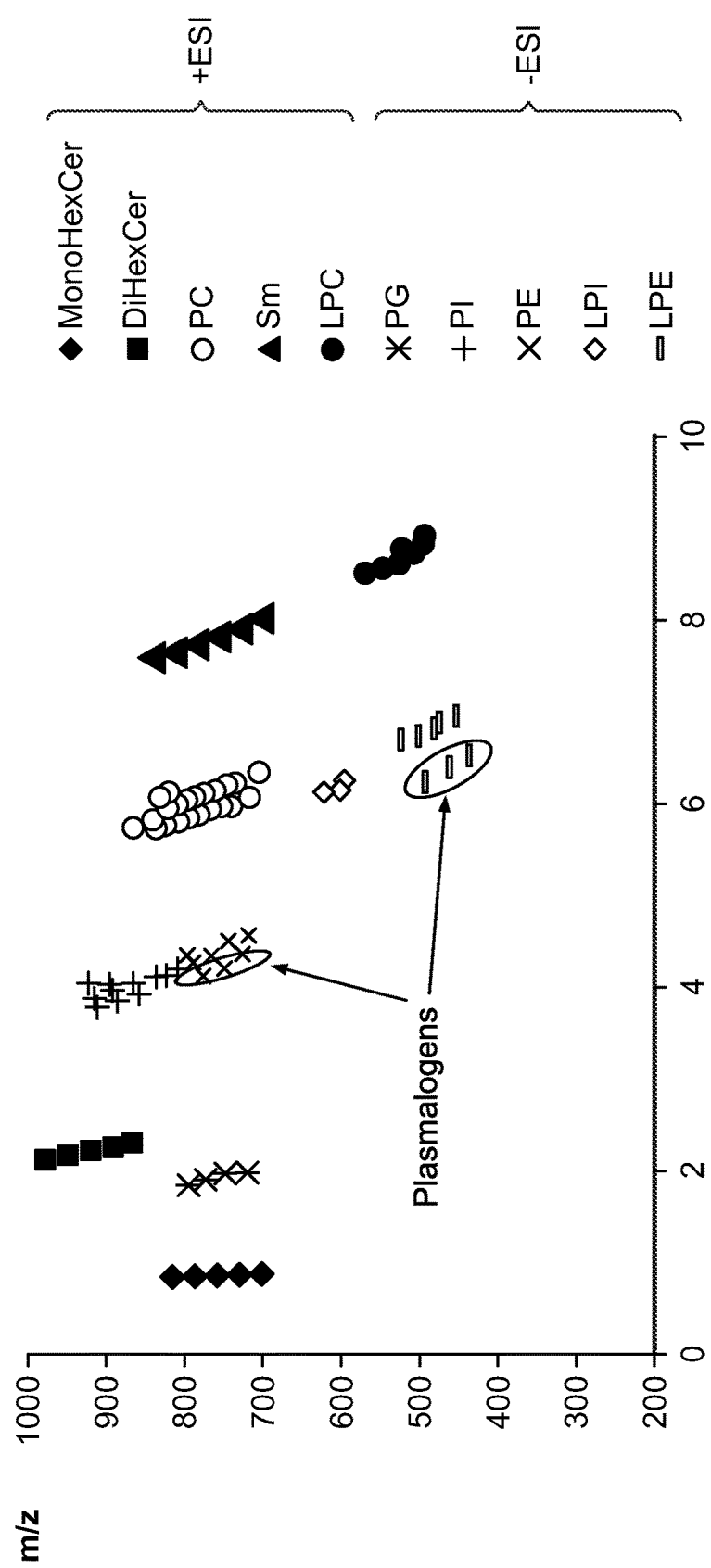
FIG. 1 is a graph showing the relationship of m/z vs. retention time obtained by the HILIC-based UHPLC method for lipids of different classes.
Figure 2A:
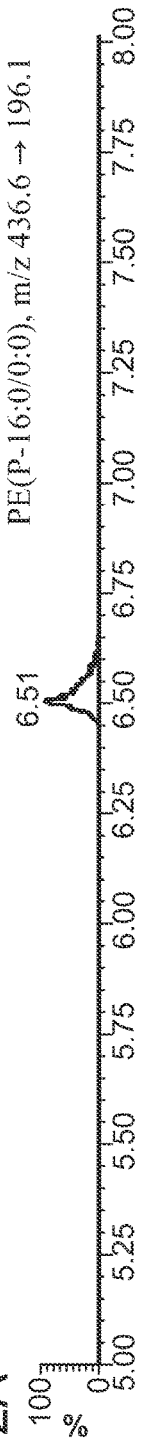
FIGS. 2 a-j) are chromatograms showing multiple reaction monitoring (MRM) traces for lyso-phosphatidylethanolamines (Lyso-PEs); the Lyso-PEs in traces a-d contain a plasmalogen. Each trace represents a specific precursor ion to fragment ion transition.
Figure 2B:
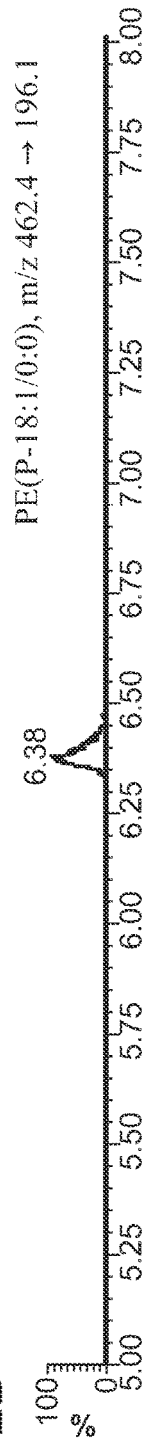
Figure 2C:
Figure 2D:
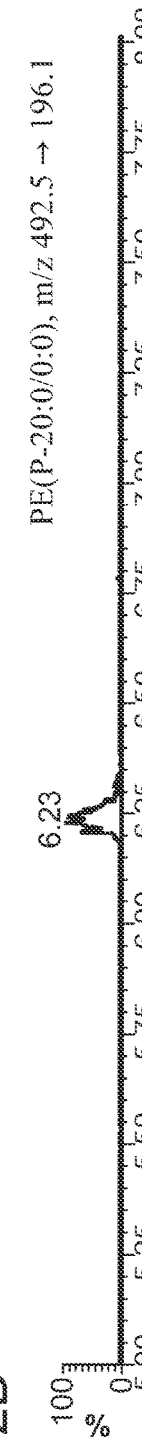
Figure 2E:
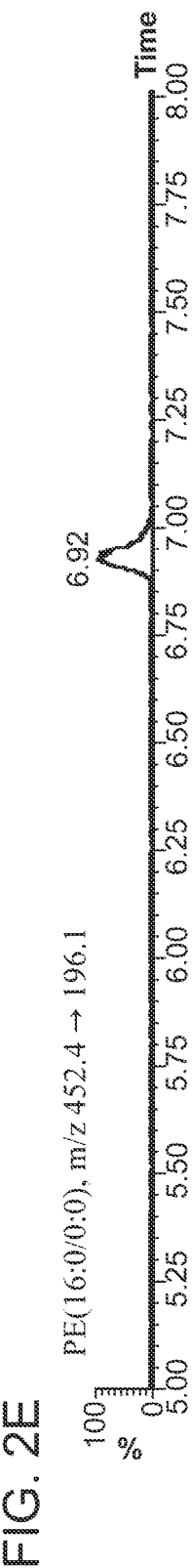
Figure 4A:
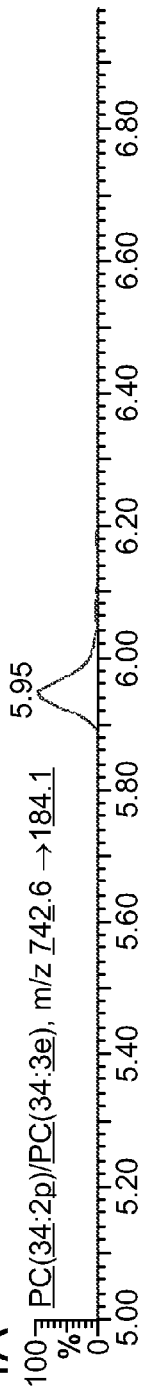
FIGS. 4 a-g) are chromatograms showing MRM traces for phosphatidylcholines (PCs): the PCs in traces a-d contain a plasmalogen or ether (and double bond). Each trace represents a specific precursor ion to fragment ion transition.
Figure 4B:
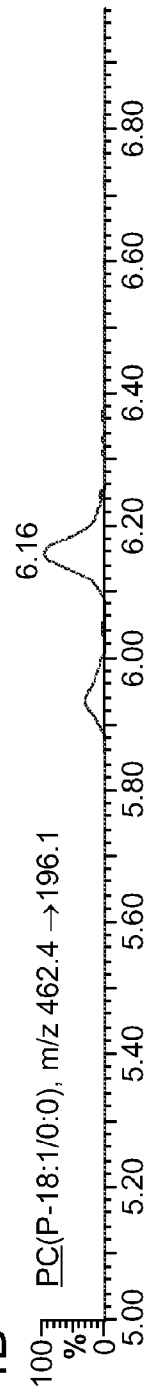
Figure 4C:
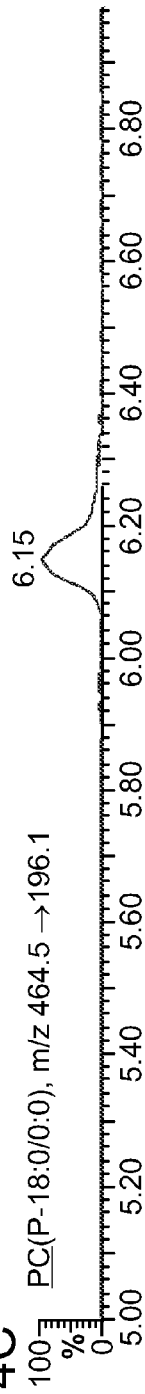
Figure 4D:
Figure 4E:
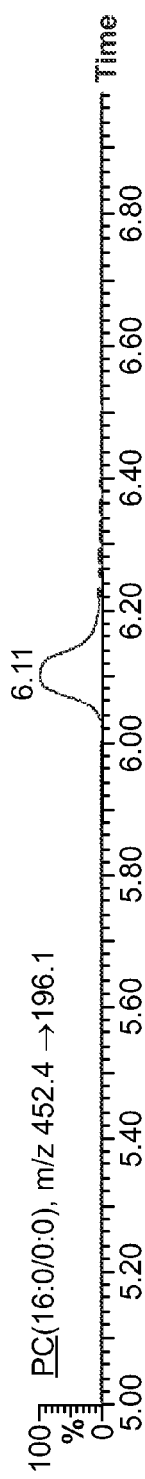
Figure 4F:
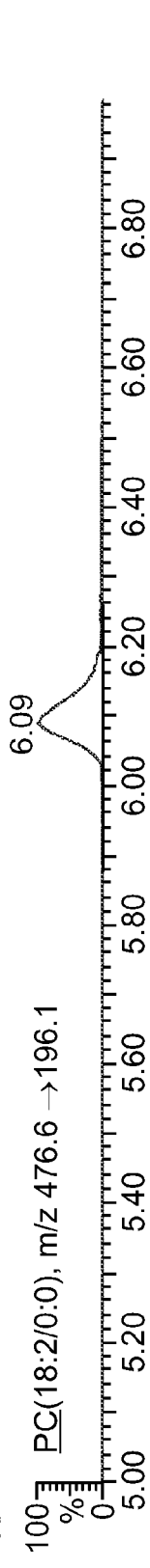
Figure 4G:
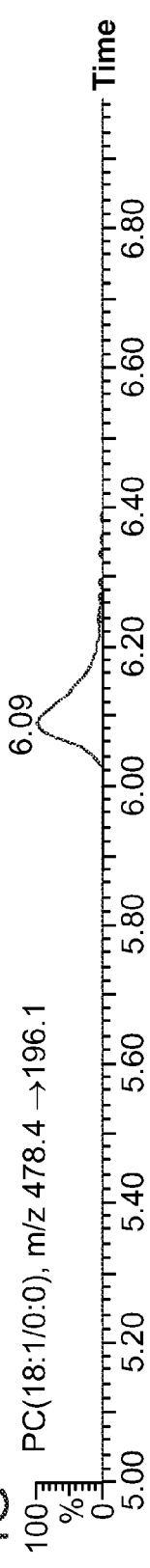

The present invention provides novel, simple, reliable and effective methods for separating various lipids from biological samples. The present invention will be more fully illustrated by reference to the definitions set forth below in the context of the following detailed description.

Definitions

As used in the specification and claims, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, an "acyl" group refers to a functional group derived by the removal of one or more hydroxyl groups from an oxoacid. The acyl group is usually derived from a carboxylic acid Therefore, it usually has the formula RCO—, where R represents an alkyl group that is attached to the CO group with a single bond.

The term "alkenyl" refers to unsaturated aliphatic groups analogous to alkyls, but which contain at least one double bond.

The term "sample" refers to any solution of a molecule or mixture of molecules that comprises at least one molecule that is subjected to extraction, separation, analysis or profiling. Particular examples include, but are not limited to, biological samples including a sample from human or animals (e.g., blood, blood plasma, urine, mucosal tissue secretions, tears, semen, and breast milk). The sample may further include macromolecules, e.g., substances, such as biopolymers, e.g., proteins, e.g., proteolytic proteins or lipophilic proteins, such as receptors and other membrane-bound proteins, and peptides. The sample may further include one or more lipid molecules.

The language "biological sample" refers to any solution or extract containing a molecule or mixture of molecules that comprises at least one biomolecule that is subjected to extraction or analysis that originated from a biological source (such as, humans and animals). Biological samples are intended to include crude or purified, e.g., isolated or commercially obtained, samples. Particular examples include, but are not limited to, inclusion bodies, biological fluids, biological tissues, biological matrices, embedded tissue samples, cells (e.g., one or more types of cells), and cell culture supernatants The language "biological fluid" as used herein is intended to include fluids that are obtained from a biological source. Exemplary biological fluids include, but are not limited to, blood, blood plasma, urine, spinal fluid, mucosal tissue secretions, tears, interstitial fluid, synovial fluid, semen, and breast milk.

As used herein, the terms "comprises," "comprising," "containing," "having," and the like can have the meaning ascribed to them under U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

The terms "analysis" or "analyzing" are used interchangeably and refer to any of the various methods of separating, detecting, isolating, purifying, solubilizing, detecting and/or characterizing biological molecules (e.g., lipids). Examples include, but are not limited to, solid phase extraction, solid phase micro extraction, electrophoresis, mass spectrometry, e.g., MALDI-MS or ESI, liquid chromatography, e.g., high performance, e.g., reverse phase, normal phase, or size exclusion, ion-pair liquid chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

The term "profiling" refers to any of various methods of analysis which are used in combination to provide the content, composition, or characteristic ratio of biological molecules (e.g., a lipid molecule) in a sample.

The term "electrophoresis" refers to any of the various methods of analyzing small molecules by their rate of movement in an electric field, i.e. based on the charge to mass ratio of the molecules. Examples include, but are not limited to, free zone electrophoresis and capillary electrophoresis.

The term "mass spectrometric detection" refers to any of the various methods of mass spectroscopy. Examples include, but are not limited to, electrospray ionization (ESI), surface desorption ionization techniques, and atmospheric pressure chemical ionization (APCI).

The language "surface desorption ionization" is intended to include mass spectrometry, such as matrix assisted laser desorption ionization (MALDI-MS), desorption ionization on silicon (DIOS), thermal desorption mass spectrometry, or surface enhanced laser desorption ionization (SELDI) where desorption ionization is accomplished on a surface, with or without a matrix assistance.

"High Purity" or "high purity chromatographic material" includes a material which is prepared form high purity precursors. In certain aspects, high purity materials have reduced metal contamination and/or non-diminished chromatographic properties including, but not limited to, the acidity of surface silanols and the heterogeneity of the surface.

"Chromatographic core" includes a chromatographic materials, including but not limited to an organic material such as silica or a hybrid material, as defined herein, in the form of a particle, a monolith or another suitable structure which forms an internal portion of the materials of the invention. In certain aspects, the surface of the chromatographic core represents the chromatographic surface, as defined herein, or represents a material encased by a chromatographic surface, as defined herein. The chromatographic surface material may be disposed on or bonded to or annealed to the chromatographic core in such a way that a discrete or distinct transition is discernable or may be bound to the chromatographic core in such a way as to blend with the surface of the chromatographic core resulting in a gradation of materials and no discrete internal core surface. In certain embodiments, the chromatographic surface material may be the same or different from the material of the chromatographic core and may exhibit different physical or physiochemical properties from the chromatographic core, including, but not limited to, pore volume, surface area, average pore diameter, carbon content or hydrolytic pH stability "Hydrophilic group" refers to a group (such as, a polar or charged functional group), that makes a molecule more soluble in water. In certain aspects, a hydrophilic group is a heterocyclic group, for example, a saturated, unsaturated or aromatic heterocyclic group. Suitable examples include nitrogen-containing heterocyclic groups such as pyrrolidonyl and pyridyl groups. In another embodiment, the hydrophilic moiety is an ether group. A hydrophilic molecule can be, for example, N-vinylpyrrolidone, 2-vinylpyridine, 3-vinylpyridine, a hydrophobic moiety, 4-vinylpyridine or ethylene oxide.

"Hydrophobic group" refers to a group in a molecule or repeating unit of a polymer that makes the molecule or unit repelled from a mass of water. The hydrophobic group can be, for example, an aromatic carbocyclic group, such as a phenyl or phenylene group, or an alkyl group, such as a straight chain or branched $C_2$-$C_{18}$-alkyl group.

The term "amino," as used herein, refers to an unsubstituted or substituted moiety of the formula —NRaRb, in which Ra and Rb are each independently hydrogen, alkyl, aryl, or heterocyclyl, or Ra and Rb, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. An "amino-substituted amino group" refers to an amino group in which at least one of Ra and Rb, is further substituted with an amino group.

The term "chiral moiety" is intended to include any functionality that allows for chiral or stereoselective syntheses. Chiral moieties include, but are not limited to, substituent groups having at least one chiral center, natural and unnatural amino-acids, peptides and proteins, derivatized cellulose, macrocyclic antibiotics, cyclodextrins, crown ethers, and metal complexes.

"Surface modifiers" include (typically) organic functional groups which impart a certain chromatographic functionality to a chromatographic stationary phase. The porous inorganic/organic hybrid materials possess both organic groups and silanol groups which may additionally be substituted or derivatized with a surface modifier.

Lipids

Lipids are essential in maintaining cell structures and play important roles in energy storage and cellular signalling. It is also known that lipids are important in the pathophysiology of diseases such as cancer, neurodegenerative diseases, infections, diabetes etc. Accordingly, the field of lipidomics has emerged when efforts have been devoted in identifying disease biomarkers and probing for disease mechanisms.

Lipids constitute a group of naturally occurring molecules that include fats, waxes, sterols, fat-soluble vitamins (such as vitamins A, D, E, and K), monoglycerides, diglycerides, triglycerides, phospholipids, and others. Major lipid categories include, such as, fatty acids, glycerolipids, glycerophospholipids, sphingolipids, saccharolipids, polyketides, sterol lipids, prenol lipids, fatty acids and their derivatives (including tri-, di-, monoglycerides, and phospholipids), as well as other sterol-containing metabolites such as cholesterol.

It is also appreciated that lipids can be classified in the following groups including, such as, monohexosyl ceramide (MonoHexCer), dihexosyl ceramide (DiHexCer), phosphatidylcholine (PC), sphingomyelin (SM), lyso-phosphatidylcholine (LPC), phosphatidylglycerol (PG), phosphatidylinositol (PI), phosphatidylethanolamine (PE), lyso-phosphatidylinositol (LPI), and lyso-phosphatidylethanolamine (LPE).

Further provided herein as examples are some of lipid structures:

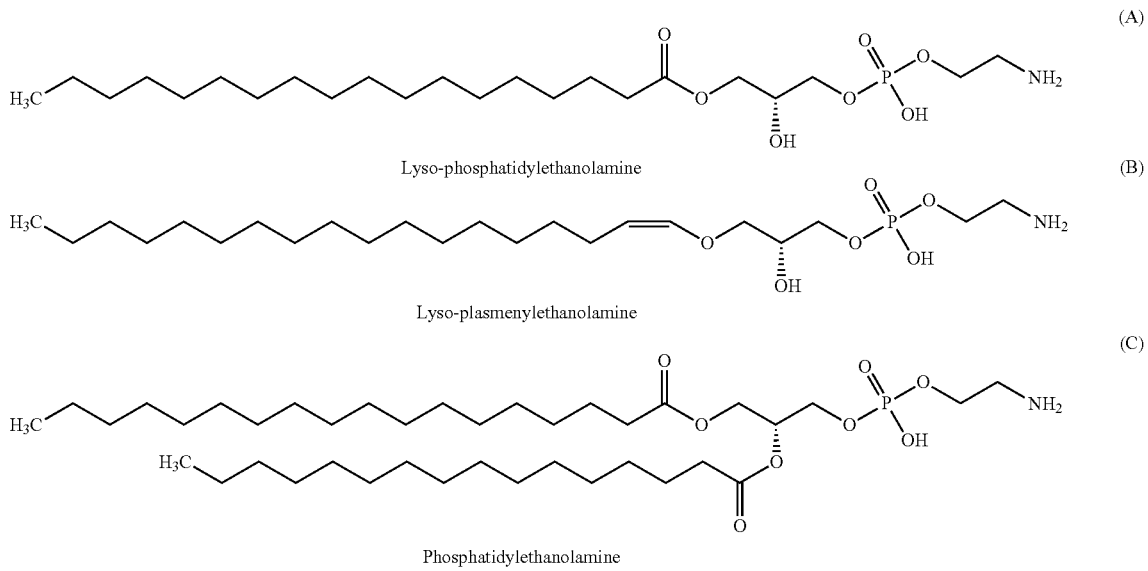

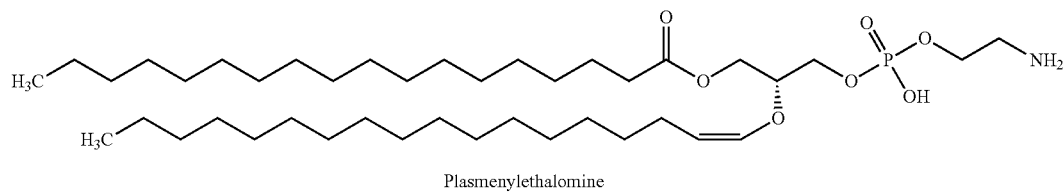

Plasmenylethalomine (D)

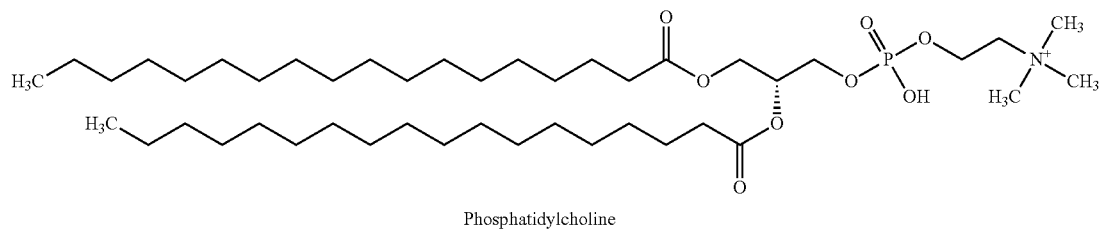

Phosphatidylcholine (E)

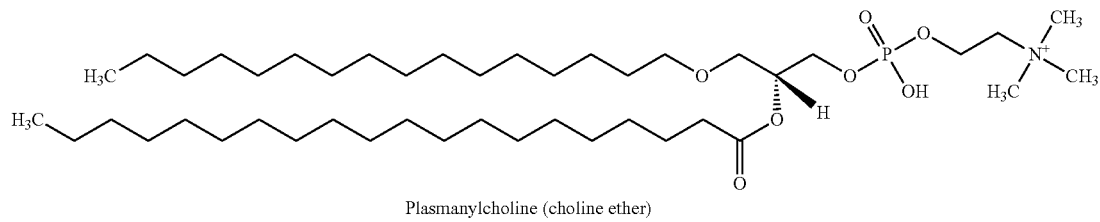

Plasmanylcholine (choline ether) (F)

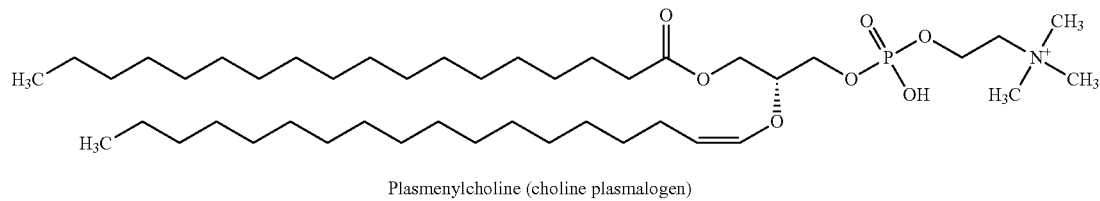

Plasmenylcholine (choline plasmalogen) (G)

Among all the lipids, mammalian phospholipids are generally assumed to contain exclusively even numbers of carbon in their acyl chains. Recently, it has been discovered that small quantities of odd-carbon number phospholipids in mammalian samples. Some odd-carbon phospholipids can have the same nominal mass, which can only be distinguished by high resolution, accurate mass spectrometers.

Ether glycerolphospholipids are known to contain an ether or vinyl ether (plasmalogen) moiety at the sn-1 position of the glycerol backbone. The following structure (b) represents a plasmalogen:

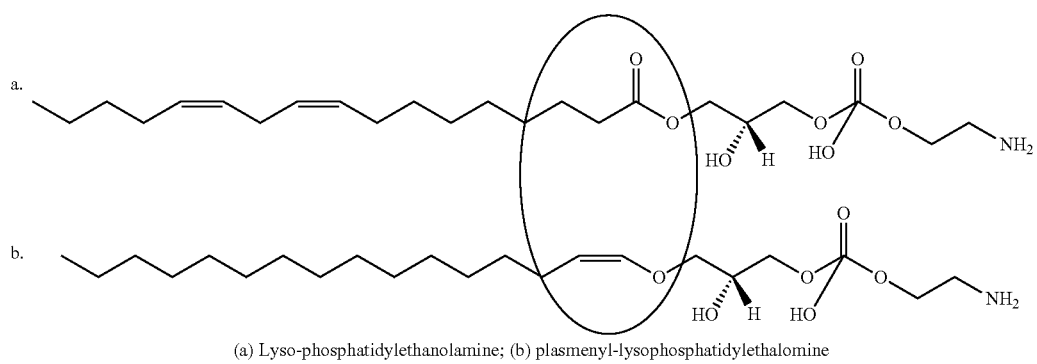

(a) Lyso-phosphatidylethanolamine; (b) plasmenyl-lysophosphatidylethalomine

Plasmalogens are enriched in the nervous, immune, and cardiovascular systems. Almost 30% of the glycerophospholipids in the adult human brain and up to 70% of myelin sheath ethanolamine glycerophospholipids are plasmalogens. Plasmenylethanolamines (ethanolamine plasmalogens) have a high propensity for adapting a non-lamellar inverse hexagonal phase, and facilitate rapid membrane fusion. Plasmalogens are generally more susceptible to oxidation than their fatty acid analogues due to the reactivity of the vinyl ether. It is now believed that reduced levels of plasmalogens are associated with several neurological disorders including Alzheimer's Disease, ischemia, spinal cord trauma, and Down syndrome.

Lipid Separation Methods

The invention provides novel, simple, reliable and effective methods for separating various lipids from biological samples. In certain embodiments, the separation is achieved, in part, based on head-groups contained in polar lipids. Specifically, the methods of the invention achieve efficient separation of phospholipids of various classes, which permits unequivocal characterization and assignment of lipid classes.

The chemical and structural complexity of different lipids, their low concentrations, and their complicated physical and chemical properties pose a major analytical challenge for their separation and characterization.

Recent advances in mass spectrometric methods have addressed partially on some of the analytical challenges associated with lipids of major classes (Hu C et al., *J Chromatogr. B Analyt Technol Biomed Life Sci.*, 2009, 15; 877(26):2836-46; Shevchenko A. et al., *Nat Rev Mol Cell Biol.* 2010, 11:593-8; Wenk M. R. *Cell,* 2010, 143:888-95; and Harkewicz R. et al., *Annu Rev Biochem.* 2011, 80:301-325).

For example, separations of certain lipids have been achieved by direct infusion method coupled to a tandem mass spectrometer (Shui G. et al., *J. Lipid Res.* 2007, 48:1976-1984; and Han X. et al., *Mass Spectrom. Rev.* 2005, 24:367-412). Nevertheless, the lack of high resolution chromatographic separation of the method means that the analyses are complicated by isobaric interferences and the dominance of high abundance components.

Recently, reversed-phase ultra-performance liquid chromatography (UHPLC) methods offer rapid and high resolution separations for separating lysophospholipids and triacylglycerides from other classes of phospholipids. As the mechanism of action in reversed-phase chromatography is based on the lipophilicity of the molecules, it is hard to achieve good class separations of all the lipids through the reversed-phase (RP) methods. Indeed, co-elution of lipids belonging to different classes in reversed-phase separations is quite common.

Normal-phase (NP) liquid chromatography has also been used for the separation of the different lipid classes. The normal-phase separation is generally based on polar head groups of the lipids. However, it has been observed that the existing NP liquid chromatography often offers poor resolution and is generally time consuming due to long elution and equilibration times. Hydrolysis of some lipids during the NP separation has also been observed.

A hydrophilic interaction chromatography (HILIC)-based method offers benefits, such as, it can use solvents typically used for reversed-phase separations, which are compatible with ESI. That is, solvents, such as, acetonitrile, methanol, and water, can be used. Further, in a HILIC method, a highly organic mobile phase (e.g., >80% acetonitrile) can be used, which in turn results in an improved electrospray ionization through efficient mobile phase desolvation and compound ionization. Nevertheless, a HILIC-based method has not yet been applied for lipid profiling.

The present inventors have discovered unexpectedly that when HILIC is coupled to UHPLC together with the use of gradient separation, enhanced chromatographic resolution and sensitivity can be achieved in lipid separations.

Thus, the invention relates, in part, to the use of a HILIC-based UHPLC method. The HILIC-based UHPLC method provides both effective class separation of lipids (especially, when compared to existing reversed-phase based methods), with a high resolution and speed (especially, compared to normal-phase based HPLC methods).

In one aspect, the invention provides a method of separating lipids of different classes from a biological sample. The method comprises steps of
  i) preparing a biological sample;
  ii) loading said biological sample onto an ultrahigh performance liquid chromatography (UHPLC) system, wherein said UHPLC system comprises a hydrophilic interaction chromatography (HILIC) column;
  iii) eluting said UHPLC system with an elution solvent; and
  iv) detecting lipids of different classes by using a detector (e.g., a mass spectrometer).

As known in the art, the detection and quantification of plasmalogens typically uses acidic hydrolysis of the plasmalogens to produce a lysophospholipid and fatty aldehyde, followed by separation using TLC or HPLC and measurement of one of the products. HPLC separation of plasmalogens can be performed after derivatization with acetic anhydride, benzoate, or iodine.

However, due to the fact that plasmalogens may easily lose information on the hydrocarbon tail groups in a mass spectrometry, plasmalogens cannot be easily distinguished from non-plasmalogen odd-carbon acyl chain phospholipids. Plasmalogens have a short half-life (about 30 minutes for PC plasmalogens), and are acid-lability. Even trace levels of acid in a separation system can catalyze the hydrolysis of plasmalogens to form a lysophospholipid and fatty aldehyde (Murphy E. J. et al., *Lipids,* 1993 28:565-568). Therefore, plasmalogens are often misidentified and/or poorly quantified.

In another aspect, the invention provides a method of separating ether glycophospholipids from a biological sample. The method comprises steps of
  i) preparing a biological sample;
  ii) loading said biological sample onto an ultrahigh performance liquid chromatography (UHPLC) system, wherein said UHPLC system comprises a hydrophilic interaction chromatography (HILIC) column;
  iii) eluting said UHPLC system with an elution solvent; and
  iv) detecting the ether glycophospholipids by using a detector (e.g., a mass spectrometer).

In certain embodiments of the invention, the UHPLC system is a Waters ACQUITY UPLC® system.

In certain embodiments, the ether glycophospholipids are plasmalogens. In one embodiment, the invention provides a HILIC-based UHPLC method for the separation of ether glycophospholipids (especially, plasmalogens) from their diacyl counterparts (or monoacyl in the case of lysophospholipids) within the same phospholipid class.

In certain embodiments of the invention, the HILIC-based UHPLC approach uses a normal phase separation system.

Normal-phase (NP) chromatography generally separates lipids of different classes based on their head groups. Ether glycophospholipids, due to lacking of the carbonyl oxygen in the sn-1 positions, have reduced hydrophilicity in the head groups. Further, the UHPLC system as used herein offers high chromatographic resolution, thus enabling the clear distinction of plasmalogens (and other ether phospholipids) from their diacyl phospholipid counterparts.

The HILIC column used in the invention can use any polar solid phase surface chemistry, including, but not restricted to simple silica, silica silanol or diol, amide, amino, anionic, cationic or zwitterionic materials, and bound to any type of packing material, e.g., monolithic, porous, solid, pellicular (fused/solid-core, semiporous) or composite beads. One example of the HILIC column is a zwitterionic sulfobetaine column. Another example provides a Waters ACQUITY BEH HILIC (1.7 µm, 2.1×100 mm) column.

In certain embodiments, the elution solvent used herein is obtained by mixing at least two mobile phases in situ. For example, a first mobile phase (A) and a second mobile phase (B) can be mixed in situ to obtain a solvent used for eluting lipids from the column. In certain embodiments, the volume ratio of the second mobile phase to the first mobile phase is in a gradient that increases during the elution step.

Alternatively, the elution solvent used herein can be prepared by pre-mixing two or more mobile phases.

The elution solvent (and the mobile phases) may comprise one or more solvents that are commonly used in chromatography systems. Exemplified solvents that can be used include, such as, ethyl acetate, chloroform, water, acetonitrile, isopropyl alcohol, methanol, ethanol, propanol, tetrahydrofuran, N,N-dimethylformamide, and dimethylsulfoxide.

In certain embodiments, each of the mobile phases for preparing the elution solvent comprises acetonitrile and water. For instance, the first mobile phase (A) comprises 95:5 by volume of acetonitrile:water, and the second mobile phase (B) comprises 50:50 by volume of acetonitrile:water.

It is believed that the invention achieves efficient separation through a quick elution and equilibration process. In certain embodiments, the volume ratio gradient of one mobile to another is accomplished within about 10 minutes. One example is that the system achieves a gradient is 0 to 20% (v/v) of mobile phase B in about 10 minutes.

In certain embodiments, the pH value of the elution solvent used herein is higher than 7 (e.g., a pH of 8.0). The elution solvent may further comprise salts, such as, ammonium acetate, and ammonium formate.

According to the invention, the detector that can be used is a mass spectrometer. Exemplified mass spectrometers include LC-MS/MS, MALDI-MS, tandem quadrupole mass spectrometer, and ESI-MS, or a combination thereof.

The methods of the invention may further include further separation and/or characterization steps of the lipids that have been separated and/or detected by using instrumental systems, such as, off-line 2D LC system, nanoUHPLC system, UHPLC system, LC-MS/MS, mass spectrometry, MALDI-MS, ESI-MS, nuclear magnetic resonance, infrared analysis, flow injection analysis, capillary electrochromatography, ultraviolet detection or a combination thereof.

The methods of the invention may be used to separate lipids from all kinds of biological samples.

The methods of the invention can be applied in separating lipids from biological samples, such as, blood, plasma, urine, body tissue, and a lipid extract from cells or tissues. The cells or tissues can be those obtained from animals, bacteria, plants, or fungi.

In general, a biological sample can be prepared by any standard means generally known in the art. In certain embodiments of the invention, lipid extracts from biological fluids (such as, plasma or serum) is typically reconstituted in chloroform/methanol, which can be diluted in acetonitrile prior to injection. Samples are picked up in a sample needle and injected to the column in a flow of buffered acetonitrile (a weak primary solvent in HILIC), where the polar lipids are retained.

Further, the biological samples may be prepared, without limitation, by the methods disclosed in Bligh E G, Dyer W J (August 1959). "A rapid method of total lipid extraction and purification". Can J Biochem Physiol 37 (8): 911-7. PMID 13671378; Krank J, Murphy R C, Barkley R M, Duchoslav E, McAnoy A (2007). "Qualitative analysis and quantitative assessment of changes in neutral glycerol lipid molecular species within cells". Meth. Enzymol. 432: 1-20; Ivanova P T, Milne S B, Byrne M O, Xiang Y, Brown H A (2007). "Glycerophospholipid identification and quantitation by electrospray ionization mass spectrometry". Meth. Enzymol. 432: 21-57; Deems R, Buczynski M W, Bowers-Gentry R, Harkewicz R, Dennis E A (2007). "Detection and quantitation of eicosanoids via high performance liquid chromatography-electrospray ionization-mass spectrometry". Meth. Enzymol. 432: 59-82; McDonald J G, Thompson B M, McCrum E C, Russell D W (2007). "Extraction and analysis of sterols in biological matrices by high performance liquid chromatography electrospray ionization mass spectrometry". Meth. Enzymol. 432: 145-70; Garrett T A, Guan Z, Raetz C R (2007). "Analysis of ubiquinones, dolichols, and dolichol diphosphate-oligosaccharides by liquid chromatography-electrospray ionization-mass spectrometry". Meth. Enzymol. 432: 117-43; Sullards M C, Allegood J C, Kelly S, Wang E, Haynes Calif., Park H, Chen Y, Merrill A H (2007). "Structure-specific, quantitative methods for analysis of sphingolipids by liquid chromatography-tandem mass spectrometry: "inside-out" sphingolipidomics". Meth. Enzymol. 432: 83-115; or Å. Frostegård, A. Tunlid and E. Bååth (August 1991). "Microbial biomass measured as total lipid phosphate in soils of different organic content". J. of Microbiological Methods 14: 151-163.

As above discussed, further detection and/or analysis of elutes from the chromatography can also be performed by instrumentation including, without limitation, off-line 2D LC system, nanoUHPLC system, UHPLC system, solid phase extraction, solid phase micro extraction, electrophoresis, mass spectrometry, e.g., LC-MS/MS, MALDI-MS or ESI, liquid chromatography, e.g., high performance, reverse phase, normal phase, or size exclusion, ion-pair liquid chromatography, gas chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

The methods of the invention are simple and effective in separating lipids by class in a similar fashion to normal-phase chromatography. Further, the methods are much faster than conventional normal-phase methods. The methods of the invention use less toxic solvents that are compatible with electrospray mass spectrometry. In certain embodiments, HILIC columns separate the lipid classes by their head groups, which can be complementary to reversed-phase separation techniques, which separate the individual lipid species by fatty acid chain length and degree of saturation. As HILIC and reversed-phase separations are orthogonal in their separations, it is believed that a HILIC column can be used as the first dimension for a more comprehensive 2D NP-RP UHPLC separation strategy.

Further, the high chromatographic resolution of UHPLC of the invention enables a rapid separation of ether glycophospholipids (especially, plasmalogens) from other lipid classes. In addition, by using mobile phases with a high pH value (e.g., pH 8), acid-catalyzed hydrolysis of ether glycophospholipids (especially, plasmalogens) can be avoided. Clearly, the methods of the invention allow accurate quantification of ether glycophospholipids (especially, plasmalogens) without the need for derivatization.

Moreover, by using tandem quadrupole MS systems for quantification, the chromatographic separation of lipids by class allows synchronization of the MRM transitions with the lipid retention times, increasing the number of data points acquired across the chromatographic peak. This therefore results in greater experimental reproducibility compared to reversed-phase methods that do not discriminate by class.

The methods of the invention may also be combined with other chromatography steps as part of a multi-dimensional UHPLC separation method. Such chromatography steps include, for example, HILIC×RP, either on-line or off-line (following fraction collection, as described), or other separation methods, such as, ion mobility.

This method can be employed on any combination of UHPLC/UHPLC and MS system, and may include any number of stages of MS. The HILIC column can use any polar solid phase surface chemistry, including, but not restricted to simple silica silanol or diol, amino or anionic, amide, cationic or zwitterionic, and bound to any type of packing material, e.g. monolithic, porous, solid, pellicular (fused/solid-core, semiporous) or composite beads.

The methods of the invention can be applied to any sample containing lipids (e.g., plasmalogens). The samples include, such as, biological fluids such as plasma, serum, urine, but also extracts from cells and tissue (particularly neural) including bacteria, plants and fungi.

Separation Systems

In certain embodiments, the systems used herein include an ultrahigh performance liquid (UHPLC) chromatography system coupled to a detector (e.g., a mass spectrometer). The UHPLC system, for example, comprises an autosampler, liquid handling pump and mixer, an analytical column (e.g., a HILIC column), and heater.

In certain embodiments, the invention employs the following instruments and conditions:
LC Conditions
LC system: Waters ACQUITY UPLC® System (a UHPLC system)
Column: Waters ACQUITY BEH HILIC 1.7 μm, 2.1×100 mm
Column temp.: 30° C.
Flow rate: 500 μL/min
Mobile phase A: Acetonitrile/Water (95:5) with 10 mM Ammonium Acetate, pH 8.0
Mobile phase B: Acetonitrile/Water (50:50) with 10 mM Ammonium Acetate, pH 8.0
Gradient: Linear, 100 to 80% A in 10 min
MS Conditions
MS system: Waters Xevo QT of MS
Ionization mode: ESI Positive/Negative
Capillary voltage: 2800 V (Positive)/1900 V (Negative)
Cone voltage: 35 V
Desolvation temp.: 500° C.
Desolvation gas: 1000 L/Hr
Source temp.: 120° C.
Acquisition range: 100 to 1200 m/z Further, the invention may use other monolithic and/or core-shell columns. These columns include, such as, those as follows:
  Merck Sequant ZIC-HILIC
  Phenomenex Kinetex core-shell 1.7 μm HILIC
  Agilent 1.8 μm ZORBAX Rapid Resolution High Definition HILIC Plus
  Fortis 1.7 μm HILIC Diol
  Ascentis Express 2.7 μm fused-core HILIC
  HALO 2.7 μm fused-core HILIC
  ChromStore 1.8 μm Polar-100, Silica, Diol, Pyridine, Imidazole HILIC UHPLC
  VisionHT 1.5 μm HILIC 120A UHPLC In one example, the HILIC separations are performed by using an ACQUITY UPLC® system (Waters, Singapore) comprising an ACQUITY BEH HILIC 1.7 μm, 2.1×100 mm analytical column. Mobile phases used are mobile phase A, 95:5 (v/v) acetonitrile:water with 10 mM ammonium acetate, pH 8.0, and mobile phase B, 50:50 (v/v) acetonitrile:water with 10 mM ammonium acetate, pH 8.0. The column temperature is maintained at 30° C., and separation achieved using a 10 minute linear gradient from 0 to 20% mobile phase B at a flow rate of 0.5 mL/min. The column was then flushed with 80% mobile phase B for 3 minutes and re-equilibrated with the starting mobile phase composition for another 3 minutes.

It is also possible to use reversed-phase separations. For example, an ACQUITY UPLC® HSS T3, 1.8 μm, 2.1×100 mm column can be used at 65° C. in the above UHPLC system. The reversed-phase mobile phases employed include mobile phase A, 40:60 (v/v) acetonitrile:water with 10 mM ammonium acetate, pH 5.0, and mobile phase B, 10:90 (v/v) acetonitrile:isopropanol with 10 mM ammonium acetate, pH 5.0, with a gradient of 40% to 100% mobile phase B in 10 minutes.

The HILIC-based UHPLC-MS method of the invention can modified by changing the mobile phase composition (such as solvent composition, and additives such as salts, buffers and pH modifiers), pH, gradient (time, shape, % A and % B, etc.), column/packing material (size, chemistry, porous/non-porous, core-shell, etc.), temperature (sample, solvent, column), pressure and flow rate, The method is scalable, for example, may be performed by nanoUHPLC.

The methods of the invention may further include a step of collecting fractions eluted from a HILIC-based system. The collected fractions can be either time fractions or class separated fractions. The fractions can be collected either manually or automated, which then can be analyzed by MALDI or used for further separation (off-line 2D LC).

EXAMPLES

The present invention may be further illustrated by the following non-limiting examples describing the methods of the invention.

Example 1

General Methods and Systems a) Chemicals

Acetonitrile and isopropanol (Optima LC/MS Grade) were obtained from Fisher Scientific (Fair Lawn, N.J.). Ammonium acetate (LC-MS Ultra, Fluka), ethanol, and citrated human plasma were obtained from Sigma-Aldrich (St. Louis, Mo.). Phospholipid standards were obtained from Avanti Polar Lipids (Alabaster, Ala.). Deionized water (>18 MΩ) was produced in-house using a Milli-Q water purification system (Millipore, Bedford, Mass.) fitted with a LC-Pak™ C18 cartridge on the outlet.

b) Lipid Extraction

100 µL of human plasma was loaded into each well of an Ostro sample preparation plate designed for selective binding of phospholipids (Waters Corp, Milford, Mass.). 800 µL of ethanol was added to each sample and mixed thoroughly by repeated aspiration using a micropipette. The mixture was drawn through the plate under 15" Hg vacuum and collected. This step was repeated with the further addition of 800 µL of ethanol and the fractions combined as the "flow through".

A 800 µL of elution solvent, 4.5:4.5:1 (v/v/v) chloroform/methanol/triethylamine was then added to each sample well and an "eluate" fraction was collected under 15" Hg vacuum. This step was repeated with the further addition of 800 µL of elution solvent bringing the total eluate fraction volume to approximately 1600 µL.

Both the eluate and flow through fractions were dried down under nitrogen and reconstituted with 200 µL 1:1 (v/v) chloroform/methanol.

c) Liquid Chromatography

HILIC separations were performed on an ACQUITY UPLC® system (Waters, Singapore) using an ACQUITY UPLC® BEH HILIC 1.7 µm, 2.1×100 mm analytical column. Mobile phases used were:

Mobile phase A, 95:5 (v/v) acetonitrile:water with 10 mM ammonium acetate, pH 8.0; and Mobile phase B, 50:50 (v/v) acetonitrile:water with 10 mM ammonium acetate, pH 8.0.

The column temperature was maintained at 30° C., and separation achieved using a 10 minute linear gradient from 0 to 20% mobile phase B at a flow rate of 0.5 mL/min. The column was then flushed with 80% mobile phase B for 3 minutes and re-equilibrated with the starting mobile phase composition for another 3 minutes.

For reversed-phase separations, an ACQUITY UPLC® HSS T3, 1.8 µm, 2.1×100 mm column was used at 65° C. in the same UHPLC system. The reversed-phase mobile phases employed were A, 40:60 (v/v) acetonitrile:water with 10 mM ammonium acetate, pH 5.0, and B, 10:90 (v/v) acetonitrile:isopropanol with 10 mM ammonium acetate, pH 5.0, with a gradient of 40% to 100% mobile phase B in 10 minutes.

d) Mass Spectrometry

Identification and confirmation of lipid species were performed on a Xevo G2 Qtof mass spectrometer (Waters, Manchester, UK) with both positive and negative electrospray ionization (ESI), in $MS^E$ mode (Plumb R. S. et al., Rapid Commmun. Mass Spectrom. 2006, 20:1989-1994). Capillary and cone voltages of 2.8 kV and 35 V were employed for positive ESI, and 1.9 kV and 45 V for negative ESI. The source and desolvation temperatures were set at 120° C. and 500° C. respectively, and the desolvation gas flow 1000 L/Hr. For $MS^E$, data were collected in two channels simultaneously; low collision energy (6 V) for precursor ions and high collision energy (20-35 V) for product ions. Mass accuracy was maintained using 2 point LockMass (leucine encephalin, m/z 556.2771 and 278.1141).

Targeted quantification of the lipids was achieved by multiple reaction monitoring (MRM), whereby specific precursor to fragment ion transitions were monitored using a Xevo TQ-S tandem quadrupole mass spectrometer (Waters, Manchester, UK) with positive-negative polarity switching. The number of transitions in each class and the timing of the transitions monitored are summarized in Table 1.

TABLE 1

Number of MRM transitions and their timings used by the two methods[†].

| | LipidClass | Number of MRM Transitions | Acquisition Period of MRMs (mins) HILIC | RP |
|---|---|---|---|---|
| Method 1 100x dilution | Monohexosyl ceramide (MonoHexCer) | 18 | 0-2 | 1-13 |
| | Dihexosyl ceramide (DiHexCer) | 16 | 2-4 | 1-13 |
| | Phosphatidylcholine (PC) | 48 | 5-7 | 1-13 |
| | Sphingomyelin (SM) | 19 | 7-9 | 1-13 |
| | Lyso-Phosphatidylcholine (LPC) | 11 | 8-10 | 0-7 |
| Method 2 No dilution | Phosphatidylglycerol (PG) | 20 | 1-3 | 0-13 |
| | Phosphatidylinositol (PI) | 27 | 3-5 | 0-13 |
| | Phosphatidylethanolamine (PE) | 34 | 3-5 | 0-13 |
| | Lyso-Phosphatidylinositol (LPI) | 11 | 5-7 | 0-13 |
| | Lyso-Phosphatidylethanol-amine (LPE) | 11 | 6-8 | 0-13 |

Total transitions, Method 1 112
Total transitions, Method 2 103

For HILIC separations, the MRM time windows were set across the range of expected elution times for each class, whereas for reversed-phase, the same MRM transitions spanned the length of the gradient. Source conditions were set at 3.0 kV capillary voltage, 450° C. desolvation temperature, 1000 L/hr desolvation gas flow, 150° C. source temperature and $3.6×10^{-3}$ mBar collision cell pressure. Data analysis and processing were performed using TargetLynx™ (Waters Corp).

Example 2

Lipid Separation from Human Plasma

Phospholipids were extracted from 100 µl of human plasma using Ostro. Briefly, plasma was drawn through an Ostro 96-well plate (Waters P/N: 186005518) with 2×800 µL of ethanol and the flow through containing ceramides, PEs, PIs and PGs collected. PCs and SMs were extracted by adding 2×800 µL of 4.5:4.5:1 (v/v/v) chloroform/methanol/triethylamine to the plate and collecting the eluate. Both fractions were dried and reconstituted with 200 µL 1:1 (v/v) chloroform/methanol.

The following separation conditions were employed:

LC Conditions:

LC System: ACQUITY UPLC® System (a UHPLC system)

Column: ACQUITY BEH HILIC 1.7 µm, 2.1×100 mm

Column Temp.: 30° C.

Mobile Phase A: Acetonitrile/Water (95:5) with 10 mM Ammonium Acetate, pH 8.0

Mobile Phase B: Acetonitrile/Water (50:50) with 10 mM Ammonium Acetate, pH 8.0

Gradient: 0-20% B/10 min

Flow Rate: 500 µL/min

MS Conditions:

MS System: Xevo™ TQ-S

Ionization Mode: ESI, +/− switching

Capillary voltage: 3.0 kV

Desolvation temp.: 450° C.

Desolvation Gas: 1000 L/hr
Source Temp.: 150° C.
Collision Cell Press.: $3.6 \times 10^{-3}$ mBar
Data Management:
MS Software: MassLynx,
Informatics: TargetLynx The different lipid classes are clearly segregated when the HILIC elution times are plotted against m/z for the polar lipids (FIG. 1). In contrast to reversed-phase separations, where the retention times increase with lipophilicity (increasing chain length and decreasing number of double bonds) (Rainville P D et al., *J. Proteome Res.* 2007; 6:552-558), the HILIC elution times decrease with increasing lipophilicity within each class of lipids (Waters Application Note 720004048). The more lipophilic diacyl phospholipids elute about 2 minutes earlier than the monoacyl lyso-phospholipids with the same head group.

Further, lysophosphatidylethanolamines and phosphatidylethanolamines are divided into two groups due to the separation of the plasmalogens from their lyso- and diacyl phospholipid analogues, as demonstrated by the MRM traces in FIG. 2.

As above discussed, in the plasmalogens, the sn-1 ester moiety is substituted with a less polar vinyl ether. The vinyl double bond effectively extends the alkenyl chain, and loss of the protruding carbonyl oxygen also increases the lipophilicity of the headgroup (Hermetter A. Comments Mol. Cell Biophys. 1988, 5:133-149). This results in a small but significant reduction in the retention times of the plasmalogens relative to their acyl phospholipid counterparts (Řezanka T. et al., *Lipids* 2011, 46:765-780).

As shown in FIG. 2, this separation is most marked for the single chained Lyso-PEs (0.5 min), than for the separation of the plasmalogens from the diacyl phosphatidylethanolamines (0.2 min.), and phosphatidylcholines (0.1 min.). It is expected that there will also be separation of the lyso-phosphatidylcholines and their plasmalogens, but there was insufficient abundance of lyso-PC plasmalogens for this to be observed in the study.

The HILIC UHPLC-MS total ion chromatograms are shown in FIGS. 3 a-b). Although the HILIC method results in a narrow spread of retention times within each class of lipids as compared to RP-UHPLC (Rainville P. D. et al., J. Proteome Res. 2007, 6:552-558), the separation between the different classes increased significantly. This is illustrated by the separation of the phosphatidylcholines (PC), sphingomyelins (SM) and lysophosphatidylcholines (LPC) in the positive ion chromatogram (FIG. 3a). The complete separation of these classes was not possible using RP-UHPLC (Castro-Perez J. M. et al., *J. Proteome Res.* 2010, 9:2377-2389).

The triacylglycerols and diacylglycerols were not expected to interact strongly with the HILIC column and thus were not observed, whereas the ceramides (Cer) eluted early in the gradient. In the negative ion mode, phosphatidylglycerols (PG), phosphatidylinositols (PI) and phosphatidylethanolamines (PE) were separated from the PCs and eluted earlier (see FIG. 3b).

In contrast to reversed-phase, where the retention times increase with lipophilicity, the HILIC elution times decrease with increasing lipophilicity (increasing chainlength and decreasing number of double bonds) within each class of lipids.

It is noted that Dihexosyl ceramides (DiHexCer) elute later than monohexosyl ceramides (MonoHexCer) of the same chain length. It is believed that the reasons are that DiHexCer are more hydrophilic than MonoHexCer, as DiHexCer contain a greater number of hydroxyls in the dihexoside headgroup. The monoacyl lyso-phospholipids elute about 2 minutes later than the diacyl phospholipids with the same head group.

Example 3

Separation of Sphingomyelins (SMs) and Phosphatidylcholines (PCs)

Identification of lipids can be performed, based on precursor masses and the corresponding fragment or neutral loss characteristic of each group of lipids. However, some groups, such as the PCs and SMs not only produce characteristic fragments of the same mass (m/z 184.0738), but they are also only separated by 1 Da, and hence their isotopes interfere with the detection and quantification of one another. This is an issue with direct infusion where there is no separation of the different lipid classes, and is also true for RP-LC separations, where the lipid classes overlap, as illustrated in FIG. 5a.

Class-distinct separation can be achieved by normal-phase HPLC methods, but typically require about an hour for efficient separation (Shui G et al., *PLoS One* 2010, 5:e11956). Thus, a 'normal-phase'-like method providing effective separation of different lipid classes on UHPLC timescales (about 10 minutes) is highly desirable.

Figure 6A:
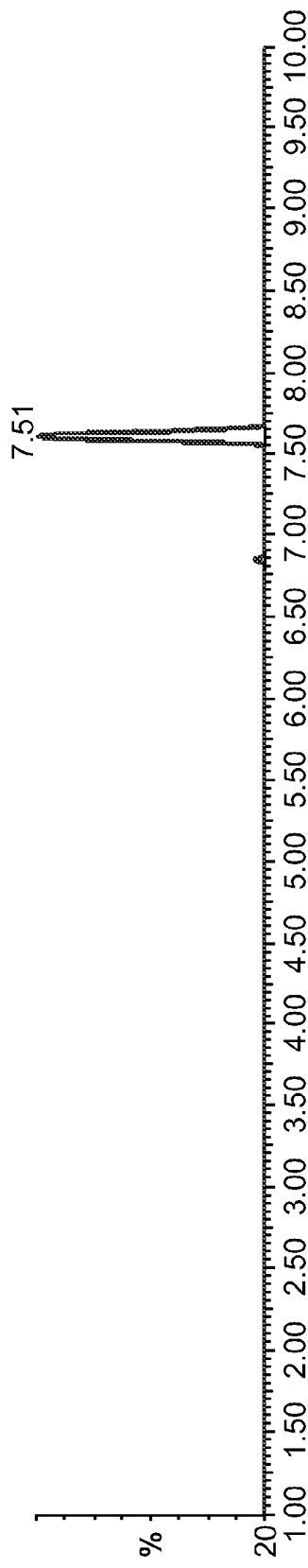
FIGS. 6 a-b) are extracted ion chromatograms with a 2 mDa window for sphingomyelin (SM) (18/18:0), m/z 731.6062, and phosphatidylcholine (PC) (32:1), m/z 732.5538.
Figure 6B:
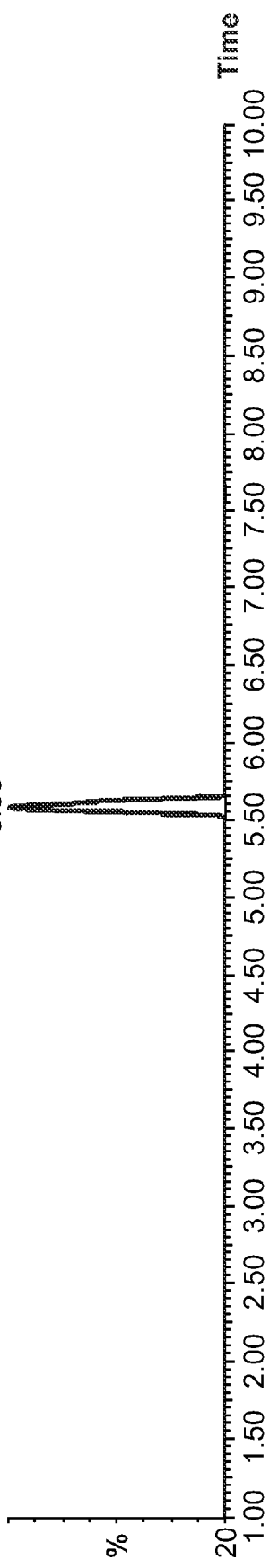

The above desired result has been achieved using HILIC, as demonstrated in FIG. 5b. The separation of PCs from SMs using the HILIC is exemplified by PC(32:1), m/z 732.5545 and SM (18/18:0), m/z 731.6069. These are closely eluting when using reversed-phase chromatography, but are separated by around 2 minutes using HILIC (FIG. 6). The separation of these two classes of lipids into distinct regions of the chromatogram allows unambiguous detection and measurement.

Using the HILIC-based UHPLC method, the SM and PC classes are well separated and therefore there is greater confidence in the accuracy and reliability of the data on the presence and abundance of the SMs.

One exception is the greater number SM species observed and with significantly greater intensities for the reversed-phase method compared to HILIC. Since PCs are significantly more abundant than SMs in plasma, isotopic interference from PCs greatly affect SM detection and measurement, and hence SMs may potentially have been greatly over-represented in the reversed-phase data.

Example 4

Quantification: HILIC Versus RP

It is known that quantitative tandem MS experiment, maintaining sufficient duty cycle to obtain good quantification limits the number of species that can be analysed simultaneously. The elution time range for each lipid class is narrow and predictable for the HILIC-based UHPLC method.

By restricting the MRM transitions to only the class(es) expected to elute in a time range, the number of transitions used at a particular time are significantly reduced. This increases the number of data points that can be acquired across the chromatographic peak, resulting in better definition and quality of the measured MRM peaks, thus improving the reliability and reproducibility of quantification. This manifests in the consistently lower relative standard deviations (% RSDs) for the peak areas measured with the HILIC approach compared to the reversed-phase method (Table 2).

TABLE 2

| Lipid Class | Species Detected | | Average Intensity | | % RSD | |
|---|---|---|---|---|---|---|
| | HILIC | Reversed Phase | HILIC | Reversed Phase | HILIC | Reversed Phase |
| LPCs | 9 | 9 | 303,741 | 332,736 | 2.1 | 4.2 |
| SMs | 15 | 19* | 11,380 | 65,036* | 4.3 | 4.4 |
| PCs | 42 | 43 | 1,133,030 | 1,736,154 | 2.2 | 4.0 |
| LPEs | 11 | 11 | 49,527 | 20,934 | 4.5 | 11.5 |
| LPIs | 1 | 0 | 1,799 | — | 15.6 | — |
| PIs | 26 | 17 | 127,011 | 33,096 | 6.0 | 13.6 |
| PEs | 30 | 24 | 74,513 | 17,648 | 6.4 | 10.8 |
| PGs | 14 | 19 | 155,422 | 105,587 | 5.0 | 8.0 |
| Cer | 9 | 6 | 28,840 | 2,337 | 13.9 | 20.1 |
| (Cer)** | (13) | — | (26,184) | — | (7.6) | — |
| Total No. Lipids Detected | 157 | 123 | — | — | — | — |
| Overall % RSD (all measurements) | — | — | — | — | 4.9 | 8.0 |

Numbers of lipid species observed by class, with the average peak area counts and % RSD for each class, as well as overall % RSD per experiment as a whole for six replicate injections by two separation method.
*Sphingomyelins detected in the reversed-phase method are difficult to distinguish from isotopic interference from phospatidylcholines, hence assignments may be incorrect
**Ceramides prepared through the Ostro[x] sample preparation route[5].

To achieve a similar number of points (as above provided) across the chromatographic peak using a reversed-phase method would require the building of a comprehensive library of lipid elution times or a complicated elution time model.

Having greater number of points across the chromatographic peak also increases the likelihood that low intensity peaks will be detected by the peak picking algorithm using the HILIC approach. The HILIC approach does detect a greater total number of lipid species than the reversed-phase approach. Each lipid class has different optimal pH for ionisation. It is thus expected that when methods use different pHs, each method shows better results for some lipids than others. Regardless of the number of detected species, the HILIC approach has consistently lower % RSDs for the peak areas than the RP method, reflecting an improved duty cycle.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

We claim:

1. A method of separating lipids of different classes from a biological sample, said method comprising steps of
   i) preparing the biological sample;
   ii) loading said biological sample onto an ultrahigh performance liquid chromatography (UHPLC) system, wherein said UHPLC system comprises a hydrophilic interaction chromatography (HILIC) column;
   iii) eluting said UHPLC column with an elution solvent, wherein the elution solvent is obtained by mixing a mobile phase A and a mobile phase B in situ, and wherein a volume ratio of the mobile phase B to the mobile phase A is at a gradient that increases during the elution step; and
   iv) detecting lipids of different classes by using a mass spectrometer.

2. The method of claim 1, wherein the mobile phase A and the mobile phase B, each independently, comprise acetonitrile and water.

3. The method of claim 2, wherein said mobile phase A comprises 95:5 by volume of acetonitrile: water, and said mobile phase B comprises 50:50 by volume of acetonitrile: water.

4. The method of claim 1, wherein said gradient is from 0 to 20% (v/v) and is completed within about 10 minutes.

5. The method of claim 1, wherein a pH value of said elution solvent is higher than 7.

6. The method of claim 5, wherein the pH value of said elution solvent is about 8.

7. The method of claim 1, wherein said elution solvent comprises ammonium acetate.

8. The method of claim 1, wherein said mass spectrometer is selected from the group consisting of LC-MS/MS, MALDI-MS, tandem quadrupole mass spectrometer, and ESI-MS, or a combination thereof.

9. The method of claim 1, wherein said biological sample is selected from the group consisting of blood, plasma, urine, body tissue, and a lipid extract from cells or tissues, wherein said cells or tissues are from animals, bacteria, plants, or fungi.

10. The method of claim 1, wherein said HILIC column is normal-phase.

11. The method of claim 10, wherein said HILIC column is a 1.7 μm, 2.1 ×100 mm ethylene bridged hybrid HILIC column.

12. The method of claim 10, wherein said HILIC column comprises a solid phase selected from the group consisting of silica, silica silanol, silica diol, amino, amide, anionic, cationic and zwitterionic materials, or a combination thereof.

13. A method of separating ether glycophospholipids from a biological sample, said method comprising steps of
  i) preparing the biological sample;
  ii) loading said biological sample onto an ultrahigh performance liquid chromatography (UPLC) system, wherein said UHPLC system comprises a hydrophilic interaction chromatography (HILIC) column;
  iii) eluting said UHPLC system with an elution solvent, wherein the elution solvent is obtained by mixing a mobile phase A and a mobile phase B in situ, and wherein a volume ratio of the mobile phase B to the mobile phase A is at a gradient that increases during the elution step; and
  iv) detecting the ether glycophospholipids by using a mass spectrometer.

14. The method of claim 13, wherein said ether glycophospholipids comprise plasmalogens.

* * * * *